US00PP21269P3

(12) United States Plant Patent
Shiozaki

(10) Patent No.: US PP21,269 P3
(45) Date of Patent: Aug. 31, 2010

(54) **VARIETY OF *DICENTRA* PLANT NAMED 'RED FOUNTAIN'**

(50) Latin Name: *Dicentra peregrina×eximia*
Varietal Denomination: Red Fountain

(75) Inventor: Akira Shiozaki, Fukagawa (JP)

(73) Assignee: Walter Blom Plants B.V., Hillegom (NL)

( * ) Notice: Subject to any disclaimer, the term of this patent is extended or adjusted under 35 U.S.C. 154(b) by 0 days.

(21) Appl. No.: 12/291,637

(22) Filed: Nov. 12, 2008

(65) Prior Publication Data

US 2010/0122389 P1 May 13, 2010

(51) Int. Cl.
*A01H 5/00* (2006.01)

(52) U.S. Cl. ..... Plt./426

(58) Field of Classification Search ..... Plt./426
See application file for complete search history.

*Primary Examiner*—Annette H Para
(74) *Attorney, Agent, or Firm*—The Webb Law Firm

(57) ABSTRACT

A new and distinct *Dicentra peregrina×eximia* plant named 'Red Fountain' with dark burgundy flowers, good vigor, a compact habit and long flowering period.

4 Drawing Sheets

Botanical classification: *Dicentra peregrina×eximia*.
Varietal denomination: 'Red Fountain'.

BACKGROUND OF THE INVENTION

The present invention comprises a new and distinct cultivar of *Dicentra peregrina×eximia* known by the varietal name 'Red Fountain'. The new variety was discovered in Hokkaido, Japan in May of 2004. The new variety has been asexually reproduced via tissue culture or cuttings, and the first date of asexual reproduction was in February of 2005 in Hokkaido, Japan. The new variety is the result of a planned breeding program cross between an unpatented, unnamed *Dicentra peregrina* plant (female parent) and an unpatented, unnamed *Dicentra eximia* plant (male parent). The purpose of the breeding program was to develop new varieties that exhibit improvements in vigor and longer flowering periods. The new variety exhibits similar form and foliage to both parents, but does have a more improved vigor, more flowers, and a longer flowering period than both parents. 'Red Fountain' exhibits similar foliage, habit, and vigor to *Dicentra peregrina×eximia* 'Candy Hearts' (U.S. Plant Pat. No. 14,692), but has a different flower color than 'Candy Hearts'. The new variety has been trial and field tested and has been found to retain its distinctive characteristics and remain true to type through successive propagations. The following characteristics distinguish 'Red Fountain' from other varieties known to the breeder:

1. Compact, more upright habit;
2. Good vigor with strong growth;
3. Strong, more rhizomatous root system; and
4. Long flowering period from late April until September.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
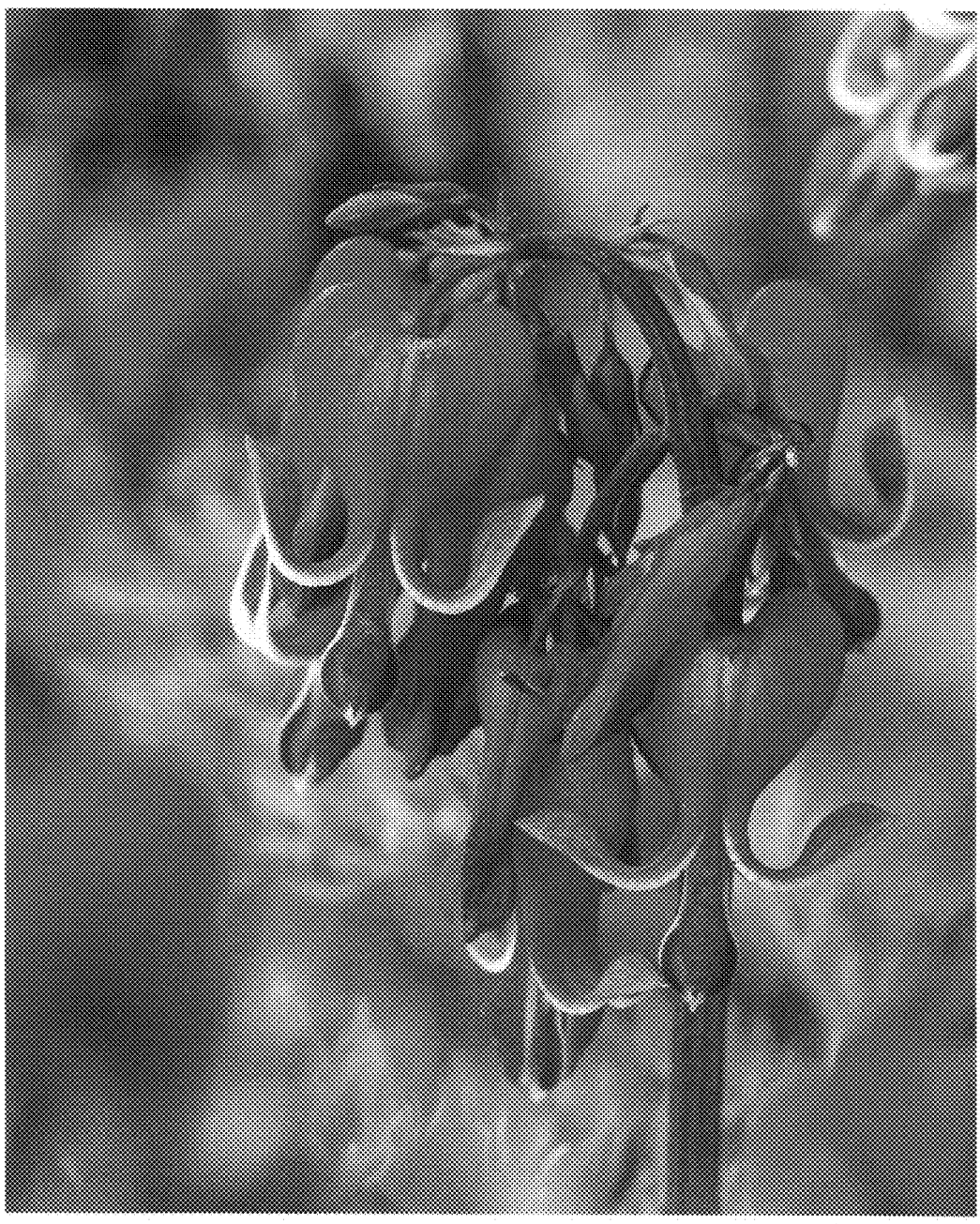
FIG. 1 is a close up view of the blossoms of the new variety.
Figure 2:
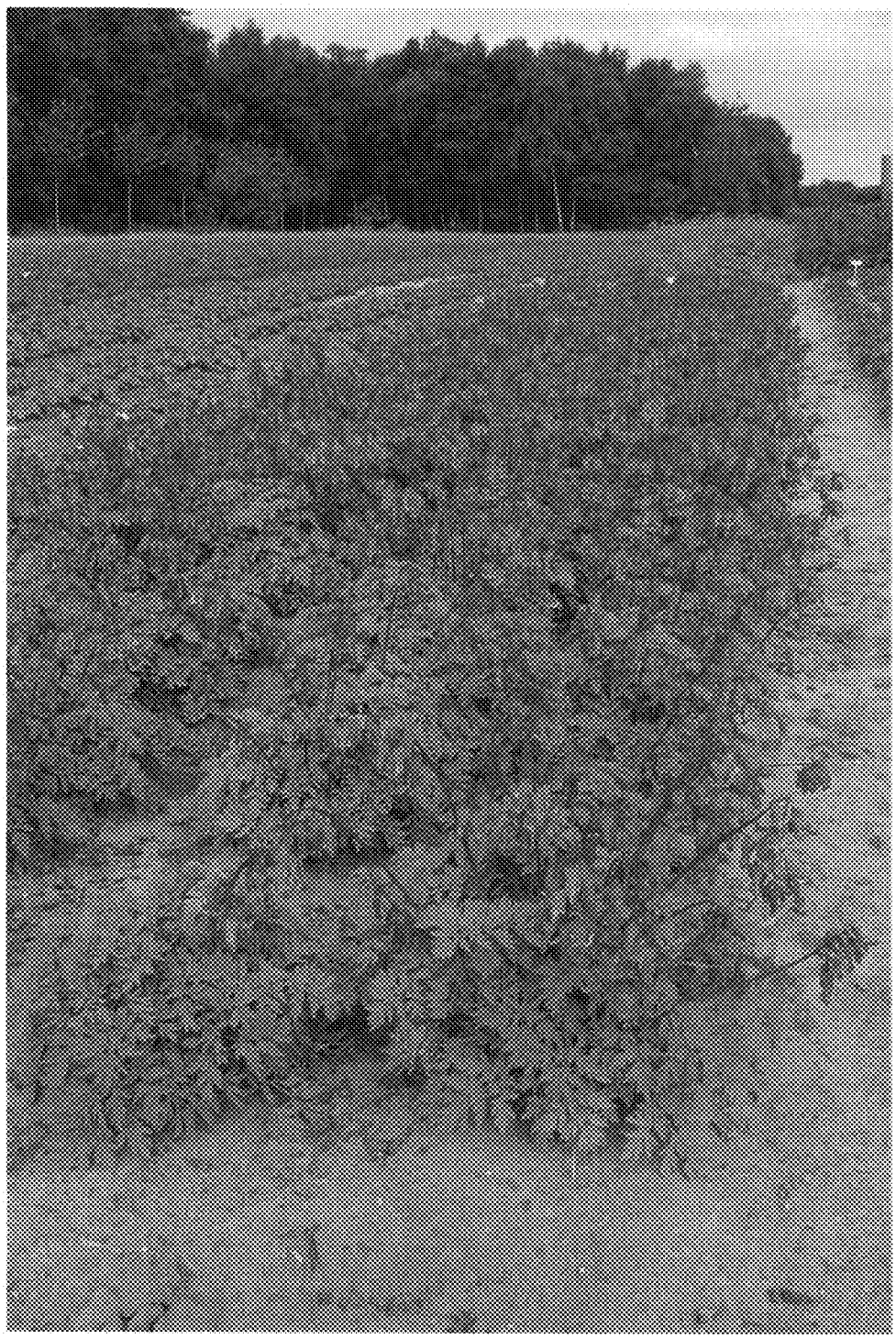
FIG. 2 is a view of a field of the new variety
Figure 3:
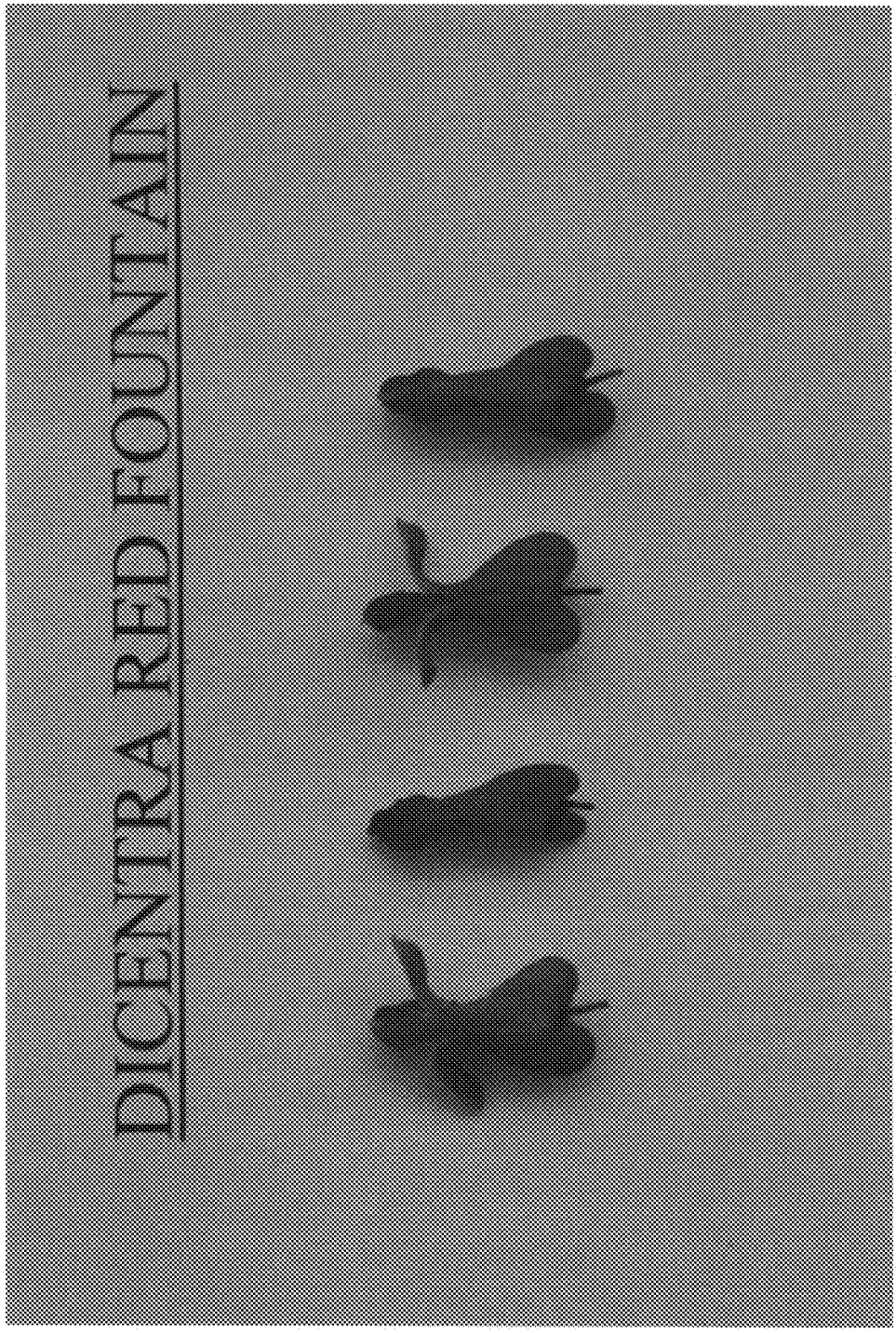
FIG. 3 is a close-up view of the blossoms of the new variety.
Figure 4:
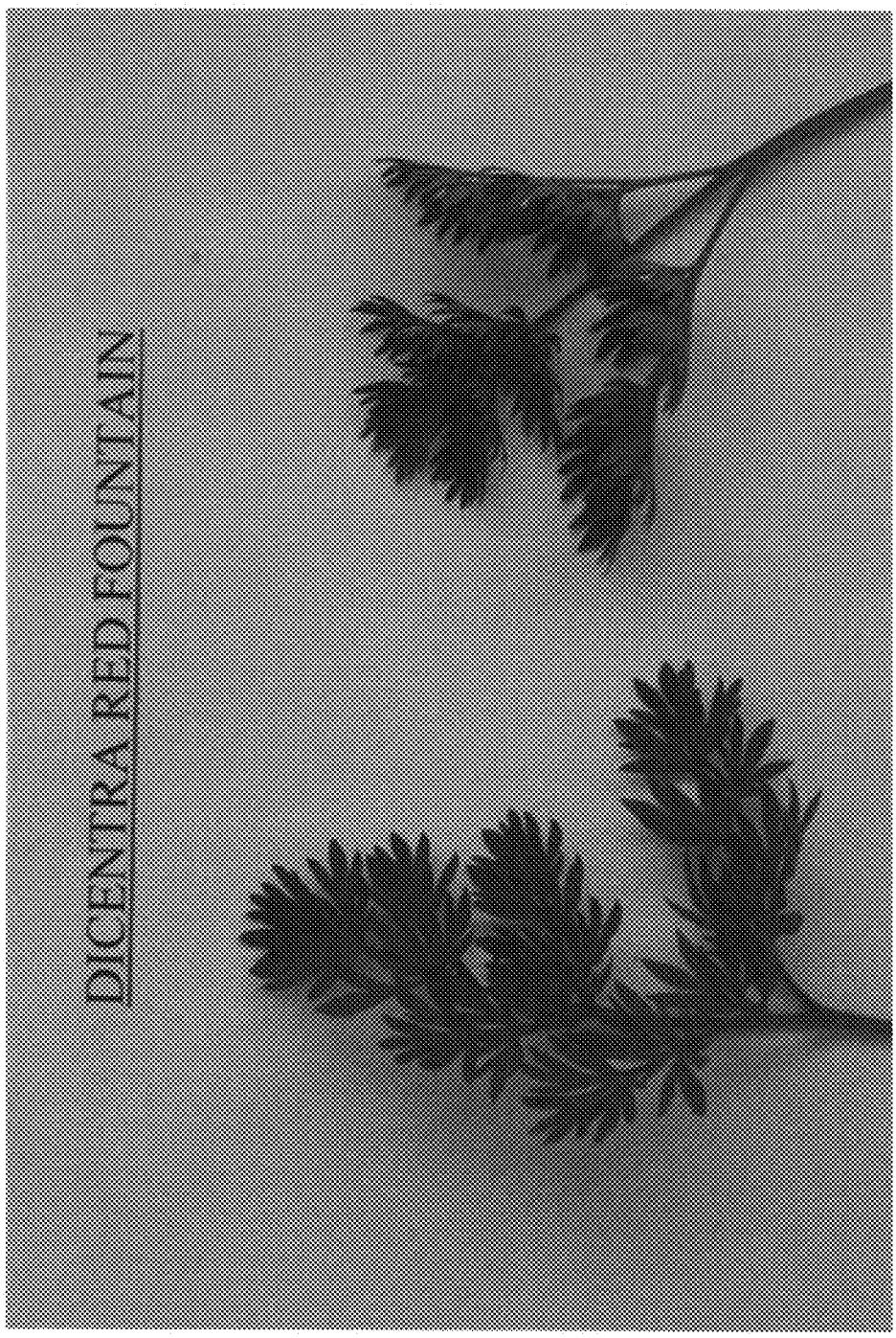
FIG. 4 is a close up view of the foliage of the new variety.

The following detailed description sets forth the characteristics of the new cultivar grown outside in the open ground with no extra fertilizer in The Netherlands. The color readings were taken in The Netherlands in natural daylight. Plants of the new cultivar were approximately four months old when described as the plugs were planted in May and the measurements were taken in early September. Color references are primarily to the R.H.S. Colour Chart of The Royal Horticultural Society of London.

PLANT

Time to initiate roots: About 21 days at about 15° C.

Time to develop roots: About 49 days at about 15° C.

Time to produce a finished flowering plant from a rooted cutting: About 70–84 days.

Rooting habit: Fine rhizomatous root system.

Form: Low spreading mounded foliage.

Stem: Not present; the foliage and flowers arise directly from the root system.

Height: Approximately 30 cm.

Plant diameter: 30–40 cm.

Vigor: Good.

Branching habit: Non-branching.

Foliage:

*Arrangement.*—Petioles arise from the base.

*Size of leaf.*—Length: 10–12 cm. Width: 10–12 cm.

*Leaflets.*—Shape of leaflet: Rounded, but deeply cut. Number: 5–7. Width: Approximately 5 cm. Length: Approximately 6 cm. Shape of apex: Acute. Shape of base: Uneven. Texture: Glabrous. Margin type: Fern-like, deeply cut. Pubescence: Upper surface: Both glabrous and glaucous. Lower surface: Both glabrous and slightly glaucous. Color: Young leaflet: Upper surface: 138A. Lower surface: 138B. Mature leaflet: Upper surface: 189A. Lower surface: 191A.

*Petiole.*—Length: Approximately 12 cm. Diameter: 3–4 mm. Color: 138A, flushed from 59A to 59B.

FLOWER

Bud: Stage of development when bud characteristics determined: Just before opening.

*Shape.*—Pitcher-shaped.

*Diameter.*—10 mm.

*Length.*—22–23 mm.

*Color.*—60A.

Natural flowering season: Mid-April until late September, depending on temperature.

Flower type and habit:

*Panicle.*—Shape: Tightly packed. Number of flowers per panicle: 16 or more flowers. Length of pedicel: 10–20 mm. Length of peduncle: 20–24 cm.

Corolla:

*Form.*—Zygomorphic; fused petals (lobed).

*Petals.*—Total number: 4 in 2 pairs. Outer pairs: Number: 1. Length: 18 mm. Width: Minimum of 4 mm to a maximum of 8 mm. Shape: Fused; cordate. Aspect: Pendant; nodding. Margin: Entire. Texture: Smooth. Color: When opening: Upper surface: 60A. Lower surface: 65D. Fully opened: Upper surface: 60A. Lower surface: 65D. Inner pairs: Number: 1. Length: 20 mm. Width: 4–5 mm. Shape: Fused tube. Aspect: Pendant; hanging. Margin: Entire. Texture: Smooth. Color: When opening: Upper surface: 60A. Lower surface: 65D. Fully opened: Upper surface: 60A. Lower surface: 65D.

Calyx:

*Form.*—Vestigial in two halves.

*Length.*—2–3 mm.

*Diameter.*—2 mm.

*Sepal shape.*—Acute.

*Sepal margin.*—Entire.

*Sepal texture.*—Glabrous.

*Sepal size.*—Length: 2–3 mm. Width: 2 mm.

*Sepal color.*—Upper surface: 59A. Lower surface: 59B.

Fragrance: Lightly fragrant.

Disease resistance: Good, slightly susceptible to Phytophora.

Temperature tolerance: Between −10° C. to +30° C.

Lasting quality: Excellent; lasting up to 3 weeks depending on weather conditions.

REPRODUCTIVE ORGANS

Stamens:

*Number.*—2 per flower.

*Filaments.*—Length: 20 mm. Fused: Yes. Color: 155C.

*Anthers.*—Shape: Triform. Length: 2 mm. Color: 17A.

*Pollen.*—Color: 17A. Amount: Little.

Pistils:

*Length.*—Approximately 20 mm. Style: Length.—11–12 mm. Color: 144B.

*Stigma.*—Shape: Rounded. Color: 144A.

Seed/fruit production: None observed.

I claim:

1. A new and distinct variety of *Dicentra peregrina*×*eximia* plant named 'Red Fountain' substantially as shown and described herein.

* * * * *